United States Patent [19]

Buckle et al.

[11] 4,248,879
[45] Feb. 3, 1981

[54] BENZOPYRANOTRIAZOLES

[75] Inventors: Derek R. Buckle, Redhill; Harry Smith, Maplehurst, both of England

[73] Assignee: Beecham Group Limited, England

[21] Appl. No.: 57,955

[22] Filed: Jul. 16, 1979

[30] Foreign Application Priority Data

Jul. 24, 1978 [GB] United Kingdom ............... 30803/78
Nov. 16, 1978 [GB] United Kingdom ............... 44719/78

[51] Int. Cl.³ .................. A61K 31/41; C07D 491/056; C07D 491/153
[52] U.S. Cl. .............................. 424/269; 260/453 A; 548/101; 548/255; 424/245
[58] Field of Search ............... 548/256, 101; 424/269, 424/245

[56] References Cited

U.S. PATENT DOCUMENTS 3,968,119  7/1976  Harnisch .............................. 548/256

FOREIGN PATENT DOCUMENTS 2310  6/1979  European Pat. Off. ................ 424/269
7508108  7/1974  Netherlands ............................ 424/269

*Primary Examiner*—Alton D. Rollins
*Attorney, Agent, or Firm*—Jacobs & Jacobs

[57] ABSTRACT

Compounds of the formula (I):

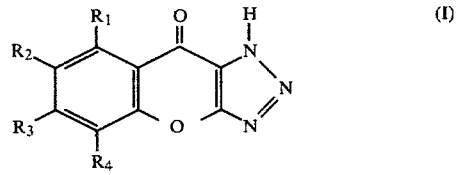

and pharmaceutically acceptable salts thereof wherein $R_1$, $R_2$, $R_3$ and $R_4$ which may be the same of different, represent hydrogen, halogen, nitro, lower alkyl, and lower alkoxy, or any adjacent two of $R_1$ to $R_4$ taken together represent an alkylene group containing from 3 to 5 carbon atoms or a 1,4-buta-1,3-dienylene group are disclosed. The compounds are useful as anti-allergic agents.

12 Claims, No Drawings

BENZOPYRANOTRIAZOLES

This invention relates to a series of benzopyranotriazoles, to a method for their preparation and their use as anti-allergic agents.

It is generally recognised that certain cells, e.g. mast cells are activated by antibody-antigen combinations and release substances which mediate an allergic response. We have discovered a novel class of 9-oxo-1H,9H-benzopyrano[2,3-d]-v-triazole derivatives which inhibit this type of antigen-induced response in mammals, and are therefore of value in the prophylaxis of diseases in which the symptoms are controlled by mediators of the allergic response. Examples of such diseases include bronchial asthma, rhinitis, hayfever and allergic eczema.

Accordingly, the present invention provides a compound of the formula (I):

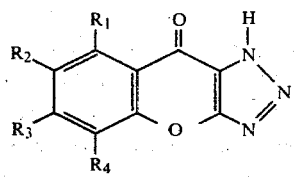

and pharmaceutically acceptable salts thereof, wherein $R_1$, $R_2$, $R_3$ and $R_4$, which may be the same of different, represent hydrogen, halogen, nitro, lower alkyl or lower alkoxy, or any adjacent two of $R_1$ to $R_4$ taken together represent an alkylene group containing from 3 to 5 carbon atoms or a 1,4-buta-1,3-dienylene group.

By lower alkyl and lower alkoxy we mean such groups containing up to six carbon atoms.

Examples of suitable lower alkyl groups which $R_1$ to $R_4$ represent include methyl, ethyl and n-propyl.

Examples of suitable lower alkoxy groups which $R_1$ to $R_4$ represent include methoxy, ethoxy and n-propoxy.

Examples of suitable halogens which $R_1$ to $R_4$ represent include fluorine and chlorine.

Where compounds of formula (I) are highly substituted, it is appreciated that substituents $R_1$ to $R_4$ are selected for steric compatability.

The triazole moiety of the compounds of formula (I) has an acidic hydrogen, and accordingly may form salts. Examples of pharmaceutically acceptable salts falling within the scope of this invention include the aluminium, alkali metal and alkaline earth metal salts such as the sodium, potassium and magnesium salts; and salts with ammonia, organic bases and amino compounds.

Within the group of compounds of general formula (I) there are a number of more readily accessible sub-groups. The first is one in which at least one of $R_1$ to $R_4$ is hydrogen and the remainder are as previously defined. An example of a compound of this type is 9-oxo-5,6,8-trimethyl-1H,9H-benzopyrano[2,3-d]-v-triazole.

The second is one where two of $R_1$ to $R_4$ are hydrogen and the remainder are as previously defined. An example of a compound of this type is 5,6-dimethyl-9-oxo-1H,9H-benzopyrano[2,3-d]-v-triazole. One preferred sub-group of compounds of formula (I) is that in which $R_1$ and $R_4$ are hydrogen and $R_2$ and $R_3$, which may be the same or different, represent methyl, ethyl or n-propyl. An example of one such compound is: 6,7-dimethyl-9-oxo-1H,9H-benzopyrano[2,3-d]-v-triazole.

The invention further provides a process for preparing a compound of formula (I) which process comprises the intramolecular cyclization of a compound of formula (II):

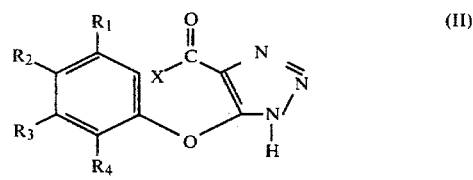

wherein $R_1$ to $R_4$ are as defined with reference to formula (I) above, and X is hydroxyl or an active substituent such that —COX is an acylating derivative, in the presence of a cyclising agent, and thereafter where desired, salifying the product so obtained.

When X is hydroxyl, the cyclisation is preferably carried out in the presence of polyphosphoric acid or phosphorous pentoxide and methane sulphonic acid. In the case of polyphosphoric acid a diluent such as acetic acid may be used.

Examples of active substituents include halides (i.e. X is halogen) paricularly the chloride and bromide. Where X is a halogen the cyclising agent is suitably a Friedel Crafts catalyst, examples of which include aluminium chloride and stannic chloride.

Where desired, the reaction may be carried out in the presence of a solvent or diluent which is inert to the reagents and products. Where the cyclizatioan is carried out using Friedel Crafts catalyst, suitable solvents or diluents include carbon disulphide and chlorinated alkanes such as methylene chloride, ethylene chloride and chloroform. When the cyclization is carried out with polyphosporic acid or phosphorous pentoxide and methane sulphonic acid, it is generally unnecessary to add a diluent.

This method when X is hydroxy is best carried out at elevated temperature i.e. above 40° C. but less than 120° C. We have found temperatures between 50° and 105° C. to be convenient.

The Friedel Crafts reaction is suitably carried out at between 0° and 40° C., preferably 20° C.

The carboxylic acids (II) where X is OH i.e. (IIa), may suitably be prepared as shown in Scheme I:

Scheme 1

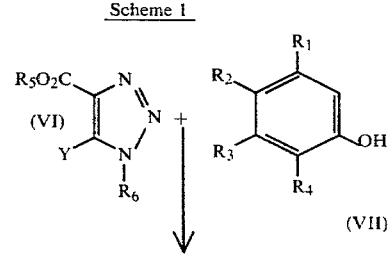

-continued

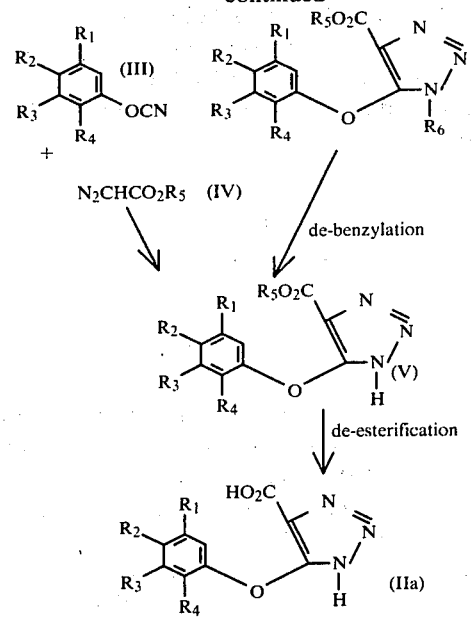

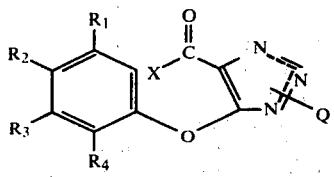

(The carboxylic acids (IIa) may be converted to an acylating derivative (II) by standard methods) in which Scheme $R_1$ to $R_4$ are as previously defined, $R_5$ is an organic group such that —$CO_2R_5$ is an ester (for example $R_5$ may be lower alkyl e.g. ethyl), $R_6$ is an hydrogenolysable benzyl group, e.g. o-methoxy, o-nitro, or p-methylbenzyl and of course benzyl itself, and Y is a leaving group, such as chlorine, bromine or iodine.

In the above Scheme, a diazo ester (IV) is condensed with an appropriate arylcyanate (III). This reaction, which may be carried out by analogy with the method of D. Martin and A. Weise, Chem. Ber. 99, 317, (1966), gives the triazole (V). Deesterification of the triazole ester (V) liberates the free carboxylic acid, (IIa).

Alternatively in the above Scheme, a substituted phenol (VII) is condensed with a triazole derivative (VI). This reaction is carried out in the presence of any base sufficient to form the phenoxide anion. We have found sodium hydride in an inert solvent such as N,N-dimethylformamide at moderate temperatures, i.e. 50°–120° C., suitably 80°–90° C., is convenient. The phenoxy derivative (VIII) is debenzylated by a standard high pressure hydrogenation method to yield the ester (V) which is de-esterified by a conventional method to yield the acid (IIa). Excluding compound (V) where $R_1$ to $R_4$ are hydrogen and $R_5$ is ethyl intermediates (II), (IIa), (V), (VI) and (VIII) are novel and provide further aspects of the invention.

We have found that often it is convenient to carry out the hereinbefore described cyclisation reaction of the compound of formula (II) to yield a desired compound of formula (I) using a compound of formula (II) in which the triazole ring has been protected. Routine de-protection of the resultant protected compound of the formula (I) yields the desired end product. Of course such protected compounds of the formula (I) are an important part of this invention, as intermediates.

Such a protected compound of the formula (II) can be represented structurally by formula (II)′:

wherein Q is a N-protecting group and the other variables are as defined.

Suitable examples of Q groups are labile benzyl groups such as $C_{1-6}$ alkoxy substituted benzyl groups, for example p-methoxybenzyl.

Such Q protecting groups may be removed from a formed compound of the formula (I) in any convenient manner, for example by acid catalysis. It is preferable to use the p-methoxybenzyl protecting group which is readily removed after the cyclisation reaction using trifluoroacetic acid, the course of the cleavage being followed by NMR spectroscopy. Suitably temperatures of around 40°–60° C. can be used, with a suitable reaction time being around 3–4 hours. Other strong acids such as methane sulphonic acid behave similarly.

On occasions it will be found that the reaction conditions for the cyclisation reaction will be sufficient to effect the necessary deprotection after cyclisation without a further, separate, reaction step being required.

It should be noted that this procedure of using a protected compound of the formula (II)′ in the cyclisation reaction is especially suited to Friedel Crafts catalysed cyclisation reactions.

The preparation of protected compounds of the formula (II)′ is generally analogous to the hereinbefore described preparation of the compounds of formula (II); for example by de-esterification of a compound of formula (V)′:

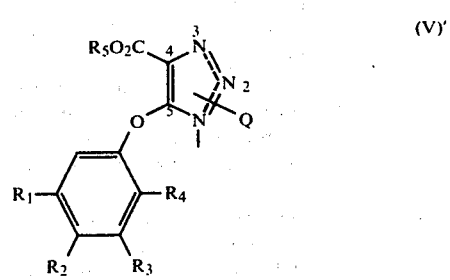

(and subsequent formation of an acylating derivative thereof if so desired)

The preparation of compounds of the formula (V)′ differs slightly depending on the position of the protecting group, but is suitably based on Scheme 2:

Scheme 2

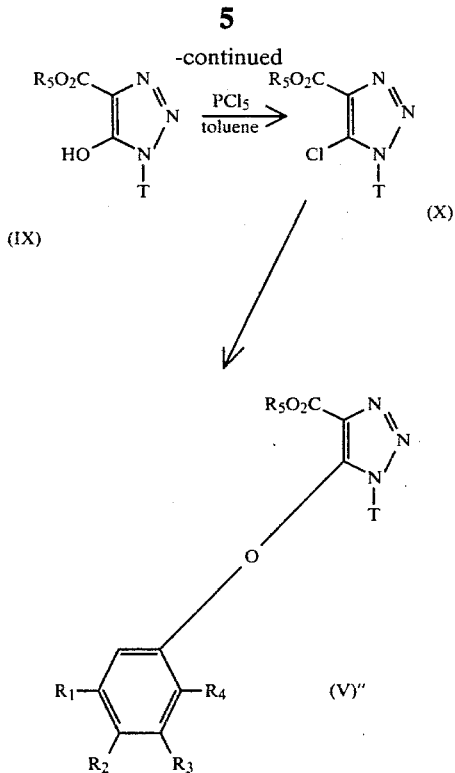

(IX) (X)

(V)″

In Scheme 2, the variable group T may be the desired protecting group Q, in which case Scheme 2 yields the desired compound of the formula (V)' with N-1 protection[i.e. at the nitrogen atom numbered 1 in formula (V)'].

To obtain the corresponding compound of the formula (V)' with N-2 and N-3 protection, then reaction Scheme 2 is followed but this time T is benzyl. Subsequently the thus formed compound of the formula (V)″ wherein T is benzyl is de-benzylated in conventional manner, and the resultant compound then reacted with an appropriate derivative, such as the halide, of the desired protecting group Q. This yields a mixture of N-2 and N-3 protected compounds of formula (V)', which can be used in the form of the mixture, or may first be separated one form the other by any of the usual separation techniques such as chromatography.

Compounds of the formula (IX) may be prepared from the corresponding azide and diethyl malonate using a similar procedure to that used by J. R. E. Hoover and A. R. Day [J. Amer. Chem. Soc., 78, 5832 (1956)].

From the preceding discussion of the preparation of the compounds of the formula (I) it will be apparent that a novel class of compounds of utility as intermediates may be represented by formula (XI):

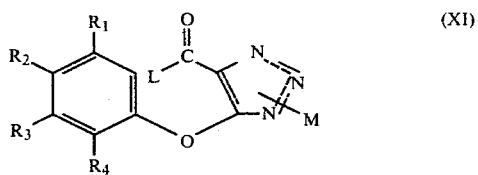

wherein $R_1$, $R_2$, $R_3$ and $R_4$ are as defined, L is hydroxy or a group such that —COL is an ester group, or an active substituent such that —COL is an acylating derivative, and M is hydrogen, benzyl, or a N-protecting group; except the compound where $R_1$ to $R_4$ and M are hydrogen and L is ethoxy. Such compounds form an important aspect of this invention.

In order to use the compounds of the invention as medicinal agents, they will be formulated into pharmaceutical compositions in accordance with standard pharmaceutical procedure.

The invention also includes a pharmceutical composition comprising a compound of formula (I) or a pharmaceutically acceptable salt thereof and a pharmaceutically acceptable carrier.

Compounds of formula (I) may be administered topically or systemically.

Topical formulations for administration to the skin include lotions and creams. Topical formulations for administration to the respiratory tract include solutions for application via a nebulizer or as an aerosol, or as a snuff or a microfine insufflatable powder. The active ingredient in an insufflatable powder has a small particle size i.e. less than 50 microns and preferably less than 10 microns. The active material is co-presented with a solid carrier such as lactose which has a particle size of less than 50 microns.

Systemic administration may be achieved by rectal, oral or parenteral administration. A typical suppository formulation comprises the active compound with a binding agent and/or lubricating agent such as gelatin or cocoa butter or other low melting vegetable waxes or fats. Typical parenteral compositions comprise a solution or suspension of the active material in a sterile aqueous carrier of parenterally acceptable oil.

Compounds of formula (I) which are active when given orally may be compounded in the form of syrups, tablets, capsules and lozenges. A syrup formulation will generally consist of a suspension or solution of the compound in a suitable liquid carrier such as ethyl alcohol, glycerine or water with a flavouring or colouring agent. Where the composition is in the form of a capsule, the solid in granular form optionally with a binding agent is encased in a gelatin shell. Where the composition is in the form of a tablet, any suitable pharmaceutical carrier routinely used for preparing solid formulations may be used. Examples of such carriers include magnesium stearate, starch, lactose, glucose, sucrose, rice flour and chalk. Preferably the composition is in unit dose form such as a pill, capsule or metered aerosol so that the patient may administer to himself a single dose.

Where appropriate, small amounts of anti-asthmatics and bronchodilators for example sympathomimetic amines such as isoprenaline, isoetharine, salbutamol, phenylephrine and ephedrine; xanthine derivatives such as theophylline and aminophylline; and corticosteroids such as prednisolone and adrenal stimulants such as ACTH may be included. As in common practice, the compositions will usually be accompanied by written or printed directions for use in the medical treatment concerned, in this case as an anti-allergic agent for treatment of, for example, asthma, hayfever or rhinitis.

In any of the foregoing formulations, a suitable dosage unit might contain from 1 to 500 mg of active ingredient. The effective dose of compound of formula (I) depends on the particular compound employed, the condition of the patient and on the frequency and route of administration, but in general is in the range of from 0.01 mg/kg/day to 50 mg/kg/day of the patient's body weight.

The following Examples illustrate the preparation and properties of some compounds within the scope of this invention.

EXAMPLE 1

(a) 5-Phenoxy-1H-v-triazole-4-carboxylic acid

A solution of ethyl 5-phenoxy-1H-v-triazole-4-carboxylate (1.365 g, 0.00575 mole, prepared by the method of D. Martin and A. Weise, Chem. Ber. 99, 317 (1966)) in 1.25 M sodium hydroxide solution (30 ml) was stirred overnight at 95° C. and then cooled. Acidification gave a white crystalline solid which was filtered off and washed well with water to give 1.073 g (90%) of acid of mp 141°–142° C. (dec.). Recrystallization from water failed to raise the mp.

$\nu_{max}$ (mull); 3130, 2600 (br), 1720, 1700, 1550 cm$^{-1}$.

$\delta$ (DMSO); 6.5 (broad exchangeable); 7.0–7.6 (complex multiplet).

(Found: C, 50.28; H, 3.74; N, 19.44; $C_9H_7N_3O_3$. 0.5 $H_2O$ requires: C, 50.47; H, 3.76; N, 19.62%).

(b) 9-Oxo-1H,9H-benzopyrano[2,3-d]-v-triazole

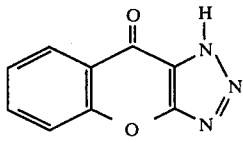

A mixture of 5-phenxoy-1H-v-triazole-4-carboxylic acid (0.5 g) in 85% polyphosphoric acid (5.8 g) was stirred at 105° C. for 24 hours and the resulting yellow solution cooled. Dilution with water (100 ml) resulted in the slow precipitation of a white solid which was filtered off and washed to give 200 mg of material of mp 246°–247° C. Recrystallisation from ethanol gave 180 mg (40%) of the title compound of mp 250°–251° C. (d).

$\nu_{max}$ (mull); 2700 (br), 1655, 1640, 1605, 1563 cm$^{-1}$.

$\delta$ (DMSO); 7.40–8.00 (3H, m); 8.27 (1H, d, J 9 Hz); Low field broad exchangeables.

(Found: C, 57.50; H, 2.90; N, 22.17; $C_9H_5N_3O_2$ requires C, 57.76; H, 2.69; N, 22.45%).

EXAMPLE 2

9-Oxo-1H,9H-benzopyrano[2,3-d]-v-triazole

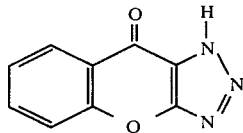

A mixture of 5-phenoxy-1H-v-triazole-4-carboxylic acid (1 g); thionyl chloride (25 ml) and 1 drop of N,N-dimethylformamide was refluxed for 2 hours and the excess thionyl chloride removed in vacuo. The residual acid chloride was dissolved in dry methylenedichloride (15 ml) and anhydrous aluminium chloride (1.63 g) added. After stirring for 3 hours at room temperature the solvent was removed and the residue treated with cold acidified water. The solid which precipitated was filtered off and recrystallized from ethanol to give 0.1 g (11%) of material of mp 249°–251° C. (dec.).

EXAMPLE 3

(a) Ethyl 5-(4-methylphenoxy)-1H-v-triazole-4-carboxylate

A solution of p-tolylcyanate (7.9 g) and ethyl diazoacetate (7.0 g) in dry dioxan (25 ml) was stirred at 100° C. for 40 hours and cooled. Excess diazo compound was destroyed by cautious addition of hydrochloric acid and water and the oily precipitate filtered off. To this precipitate was added concentrated hydrochloric acid (80 ml) and the mixture was warmed at 50° C. for 2–3 minutes, filtered, and the filtrate diluted with four volumes of water. The solid which precipitated was filtered off and recrystallized from aqueous ethanol to give 1.32 g (18%) of material of mp 94°–97° C.

$\nu_{max}$(mull); 3200, 1718, 1685 cm$^{-1}$.

$\delta$ (CDCl$_3$); 1.30 (3H, t, J 7 Hz); 2.30 (3H, s); 4.39 (2H, q, J 7 Hz); 7.10 (4H, m); 1 low field broad exchangeable proton.

(Found: C, 58.36; H, 5.42; N, 17.01; $C_{12}H_{13}N_3O_3$ requires: C, 58.29; H, 5.30; N, 16.99%).

(b) 5-(4-Methylphenoxy)-1H-v-triazole-4-carboxylic acid

Hydrolysis of ethyl 5-(4-methylphenoxy)-1H-v-triazole-4-carboxylate (1.32 g) as described in example 1a gave 1.00 g (86%) of title acid of mp (aqueous ethanol) 146°–147° C. (dec.).

$\nu_{max}$(mull); 3200, 2650 (br); 1725, 1705, 1550, 1510 cm$^{-1}$.

$\delta$ (DMSO): 2.30 (3H, s); 7.10 (1H, AB quartet, J 9.4 Hz, $\Delta\nu$ 13.6 Hz); low field exchangeable protons.

(Found: C, 52.86; H, 4.22; N, 18.56; $C_{10}H_9N_3O_3$.0.5 $H_2O$ requires: C, 52.63; H, 4.42; N, 18.41%)

(c) 7-Methyl-9-oxo-1H,9H-benzopyrano[2,3]-v-triazole

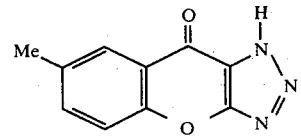

Cyclisation of 5-(4-methylphenoxy)-1H-v-triazole-4-carboxylic acid (0.7 g) with polyphosphoric acid (11 g) over 48 hours at 80° C. gave 0.44 g (69%) of product of mp (EtOH) 252°–255° C. (dec.).

$\nu_{max}$(mull): 2800 (broad); 1648, 1645, 1618, 1550 cm$^{-1}$.

$\delta$ (DMSO): 2.43 (3H, s); 7.62 (2H, s); 7.97 (1H, s).

(Found: C, 59.50; H, 3.71; N, 20.63: $C_{10}H_{17}N_3O_2$ requires: C, 59.70; H, 3.51; N, 20.89%).

EXAMPLE 4

(a) Ethyl 1-benzyl-5-(4-methoxyphenoxy)-v-triazole-4-carboxylate

Sodium hydride (0.522 g; 0.0218 mole) was added portionwise to a solution of 4-methoxyphenol (2.70 g; 0.0218 mole) in dry N,N-dimethylformamide followed by a solution of ethyl 1-benzyl-5-chloro-v-triazole-4-carboxylate (5.72 g; 0.0216 mole) in N,N-dimethylformamide (5 ml). The reaction mixture was stirred at 90° C. for two days and the solvent removed in vacuo. Water and ether were added to the residue and the phases separated. The ethereal phase was washed with aqueous sodium hydroxide solution, then water and dried (MgSO$_4$). Evaporation gave a white solid which was recrystallized from ethanol to give 5.382 g (71%) of material of mp 78°–79° C.

$\nu_{max}$(mull): 1715. 1585, 1500 cm$^{-1}$.

δ (CDCl$_3$): 1.10 (3H, t, J 7.1 Hz); 3.70 (3H, s); 4.15 (2H, q, J 7.1 Hz); 5.37 (2H, s); 6.70 (4H, s); 7.25 (5H near singlet).

(Found: C, 64.77; H, 5.37; N, 11.96; C$_{19}$H$_{19}$N$_3$O$_4$, requires; C, 64.58; H, 5.42; N, 11.89%).

(b) Ethyl 5-(4-methoxyphenoxy)-1H-v-triazole-4-carboxylate

Hydrogenation of a solution of ethyl 1-benzyl-5-(4-methoxy phenoxy)-v-triazole-4-carboxylate (2.84 g) in ethanol (300 ml) using 10% palladinized charcoal (280 mg) for 3 hours at 80° C. and 900 psi afforded 1.778 g (84%) of the debenzylated material of mp (ethanol-water) 111°–112° C.

$\nu_{max}$(mull): 3155, 1685, 1525, 1500 cm$^{-1}$.

δ (CDCl$_3$): 1.38 (3H, t, J 7 Hz); 3.82 (3H, s); 7.02 (4H, AB quartet), 1 low field exchangeable proton.

(Found: C, 54.94; H, 5.06; N, 16.05; C$_{12}$H$_{13}$N$_3$O$_4$ requires; C, 54.75; H. 4.98; N, 15.96%)

(c) 5-(4-Methoxyphenoxy)-1H-v-triazole-4-carboxylic acid

Hydrolysis of ethyl 5-(4-methoxyphenoxy)-1H-v-triazole-4-carboxylate (2.00 g; 0.0076 mole) as described in example 1a afforded 1.72 g (95% ) of the title acid of mp (water) 140° C. (dec.).

(Found: C, 49.46; H, 3.91; N, 17.08; C$_{10}$H$_9$N$_3$O$_4$ 0.5 H$_2$O requires: C, 49.18; H, 4.13; N, 17.21%).

(d) 7-Methoxy-9-oxo-1H,9H-benzopyrano[2,3-d]-v-triazole

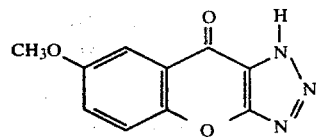

A mixture of 5-(4-methoxyphenoxy)-1H-v-triazole-4-carboxylic acid (1.5 g) and 85% polyphosphoric acid (15 g) was heated at 80° C. for 48 hours and the cooled product poured into ice water. After neutralization of the bulk of the phosphoric acid with sodium hydroxide the solution was extracted with ethyl acetate and the dried (MgSO$_4$) extracts evaporated to an oily solid. Trituration with dry ether gave the title compound as a crystalline solid. Recrystallization from ethanol gave 30 mg of product of mp 256°–258° C. (dec.).

$\nu_{max}$(mull): 3150 (br), 1675, 1650, 1615, 1550, 1475 cm$^{-1}$.

(Found: C, 54.52; H, 3.17; N, 18.20; C$_{10}$H$_7$N$_3$O$_3$.0.25 H$_2$O requires: C, 54.24; H, 3.30; N, 18.98%).

EXAMPLE 5

(a) Ethyl 1-benzyl-5-(2,3-dimethylphenoxy)-v-triazole-4-carboxylate

Reaction of 2,3-dimethylphenol (4.27 g; 0.035 mole) with ethyl 1-benzyl-5-chloro-v-triazole-4-carboxylate (9.3 g; 0.035 mole) in N,N-dimethylformamide (80 ml) as described in Example 4a, afforded 8.42 g (69%) of the title compound of mp (aqueous ethanol) 75°–76° C.

$\nu_{max}$(mull): 1735, 1560 cm$^{-1}$.

δ (CDCl$_3$): 1.03 (3H, t, J 7 Hz); 2.21 (3H, s); 2.29 (3H, s); 4.10 (2H, q, J 7 Hz); 5.34 (2H, s); 6.12 (1H, m); 6.83 (2H, m); 7.24 (5H, s).

(Found: C, 68.41; H, 6.17; N, 11.92; C$_{20}$H$_{21}$N$_3$O$_3$ requires: C, 68.36; H, 6.02; N, 11.96%).

(b) Ethyl 5-(2,3-dimethylphenoxy)-1H-v-triazole-4-carboxylate

A solution of ethyl 1-benzyl-5-(2,3-dimethylphenoxy)-v-triazole-4-carboxylate (4 g) in ethanol (400 ml) was hydrogenated at 100° C. and 1000 psi using 10% palladium charcoal catalysis to yield 2.243 g (76%) of triazole of mp (aqueous ethanol) 99°–100° C.

$\nu_{max}$(mull): 3260, 1698, 1530 cm$^{-1}$.

δ (CDCl$_3$): 1.30 (3H, t, J 7 Hz); 2.18 (3H, s); 4.38 (2H, q, J 7 Hz); 7.00 (3H near singlet); 1 low field exchangeable proton.

(Found: C, 59.96; H, 5.58; N, 15.94: C$_{13}$H$_{15}$N$_3$O$_3$ requires; C, 59.76; H, 5.79; N, 16.08%).

(c) 5-(2,3-Dimethylphenoxy)-1H-v-triazole-4-carboxylic acid

Hydrolysis of ethyl 5-(2,3-dimethylphenoxy)-1H-v-triazole-4-carboxylate (2.1 g) with aqueous sodium hydroxide (40 ml of 1.25 M) as described in example 1a gave 1.43 g (76%) of material of mp (water) 132° C. (dec.).

(Found: C, 52.56; H, 5.44; N, 16.34; C$_{11}$H$_{11}$N$_3$O$_3$ requires: C, 52.59, H, 5.22; N, 16.72%).

(d) 5,6-Dimethyl-9-oxo-1H,9H-benzopyrano[2,3-d]-v-triazole

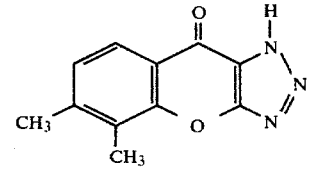

Cyclisation of 5-(2,3-dimethylphenoxy)-1H-v-triazole-4-carboxylic acid (1.43 g) with 85% polyphosphoric acid (11 g) at 80° C. overnight gave 0.863 g (65%) of the benzopyranotriazole of mp (ethanol) 265°–267° C. (dec.).

$\nu_{max}$(mull): 3450, 3360, 2600 (br), 1670 cm$^{-1}$.

δ (DMSO) 2.4 (6H, s); 7.61 (2H, AB quartet. J 8.1 Hz, Δν39 Hz). Three broad exchangeable protons (hydrate).

EXAMPLE 6

(a) Ethyl 1-benzyl-5-(3,4-dimethylphenoxy)-v-triazole-4-carboxylate

To a solution of sodium 3.4-dimethylphenoxide (from 3,4-dimethylphenol [4.27 g, 0.035 mole] and sodium hydride [1.66 g of a 50% dispersion in mineral oil, 0.035 mole, ether washed]) in dry N,N-dimethylformamide (80 ml) was added a solution of ethyl 1-benzyl-5-chloro-v-triazole-4-carboxylate (9.3 g, 0.035 mole) in dry N,N-dimethylformamide (5 ml). The mixture was stirred at 80°–90° C. for 24 hrs and the solvent removed in vacuo.

The residue was partitioned between water and ether and the organic phase separated, washed with dilute sodium hydroxide and water and dried (MgSO$_4$). Evaporation of the solvent afforded a dark solid which on recrystallization from aqueous ethanol after charcoalization, gave 9.39 g (75%) of material of mp 65°–66° C., $\nu_{max}$(mull) 1710, 1570 cm$^{-1}$; δ (CDCL$_3$) 1.13 (3H, t, J 7.1 Hz); 2.14 (3H, s); 2.19 (3H, s); 4.20 (2H, q, J 7.1 Hz); 5.39 (2H, s); 6.55 (2H, m); 7.0 (1H, m); 7.28 (5H, split s). (Found; C, 68.28; H, 6.17; N, 11.86; C$_{20}$H$_{21}$N$_3$O$_3$ requires; C, 68.36; H, 6.02; N, 11.96%.

(b) Ethyl 5-(3,4-dimethylphenoxy)-1H-v-triazole-4-carboxylate

Hydrogenation of a solution of ethyl 1-benzyl-5-(3,4-dimethylphenoxy)-v-triazole-4-carboxylate (9.39 g) in ethanol (400 ml) over 10% palladinized charcoal (0.8 g) for 2–3 hrs at 100° C. and 1000 psi afforded the title compound which was isolated by evaporation of the filtered solution and recrystallization of the residue from toluene-petrol. Yield 4.44 g (64%) mp 64°–66° C., $\nu_{max}$(mull) 3200, 1685, 1530 cm$^{-1}$; δ (CDCl$_3$), 1.31 (3H, t, J 6.8Hz); 2.20 (6H, s); 4.40 (2H, q, 6.8Hz); 6.80–7.30 (3H,m); 1 low field broad exchangeable proton. (Found; C, 59.92; H, 5.80; N, 16.14; C$_{13}$H$_{15}$N$_3$O$_3$, requires; C, 59.76; H, 5.79; N, 16.08%).

(c) 5-(3,4-Dimethylphenoxy)-1H-v-triazole-4-carboxylic acid

Hydrolysis of ethyl 5-(3,4-dimethylphenoxy)-1H-v-triazole-4-carboxylate (4.4 g; 0.0169 mole) with 1.25 M sodium hydroxide solution (36 ml) at 70°–80° C. over 5 hrs gave the title acid which was isolated in 98% yield as a white crystalline solid on acidification of the cooled solution. Recrystallization from aqueous ethanol gave material of mp 144°–145° C. (dec); $\nu_{max}$(mull) 3260, 3230, 1760 cm$^{-1}$; δ (DMSO) 2.09 (6H, s); 3.00 (3H, m). Mid field exchangeable protons. (Found: C, 56.82; H, 4.93; N, 18.08; C$_{11}$H$_{11}$N$_3$O$_3$, requires; C, 56.65; H, 4.75; N, 18.02%).

(d) 6,7-Dimethyl-1H,9H-benzopyrano[2,3-d]-v-triazole

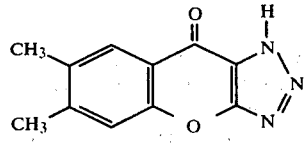

and (e) 7,8-dimethyl-1H,9H-benzopyrano[2,3-d]-v-triazole

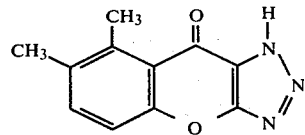

Phosphorous pentoxide (10 g) was dissolved in 98% methanesulphonic acid (45 g) at 60° C. and to this mixture was added 5-(3,4-dimethylphenoxy)-1H-v-triazole-4-carboxylic acid (1.5 g). The resulting solution was stirred at 60° C. for 24 hrs, cooled and diluted with water. After neutralization of the bulk of the acid with 2.5 M sodium hydroxide solution the isomeric products were extracted into ethyl acetate. The extracts were washed well with water, dried (MgSO$_4$) and evaporated to give 1.32 g (95%) of a 1:1 mixture of the title compounds of mp 204° C. (dec). Multiple recrystallization from ethanol gave the 6,7-dimethyl isomer as the least soluble compound mp 280°–283° C. (dec); δ (DMSO) 2.35 (3H, s); 2.39 (3H, s); 7.54 (1H, s); 7.94 (1H, s). (Found; C, 61.04; H, 3.91; N, 19.36; C$_{11}$H$_9$N$_3$O$_2$ requires; C, 61.39; H, 4.22; N, 19.52%).

Chromatographic separation of the enriched 7,8-dimethyl fractions on silica eluting with 5% methanol in chloroform gave pure samples of this isomer of mp (MeOH) 249° C. (dec), $\nu_{max}$ (KBr) 1656, 1595, 1560 cm$^{-1}$; δ (DMSO), 2.32 (3H, s); 2.76 (3H, s); 4.00 (broad exchangeables); 7.52 (2H, AB quartet, J 9 Hz; Δν 17 Hz). M+ 215.0684; C$_{11}$H$_9$N$_3$O$_2$.

(Found: C, 61.62; H, 4.11; N, 19.42; C$_{11}$H$_9$N$_3$O$_2$ requires: C, 61.39; H, 4.22; N, 19.52%).

EXAMPLE 7

(a) Ethyl 1-benzyl-5-(2,3,5-trimethylphenoxy)-v-triazole-4-carboxylate

50% Sodium hydride dispersed in oil (3.59 g; 0.075 mole) was added portionwise to a solution of 2,3,5-trimethylphenol (10.22 g; 0.075 mole) in dry N,N-dimethyl formamide (160 cm$^3$). The reaction was stirred at ambient temperature for 0.5 hour. Ethyl 1-benzyl-5-chloro-v-triazole-4-carboxylate (19.93 g; 0.075 mole) was added and the reaction mixture stirred at 95° C. for 28 hours. The reaction was cooled and the solvent removed in vacuo. Water and ether were added to the residue and the phases separated. The ethereal phase was washed with aqueous sodium hydroxide solution, then water and dried (MgSO$_4$). Evaporation gave a red oil, which crystallized overnight, the crude material was recrystallized from ethanol/water to give 15.0 g (55%) of cream, white solid mp 75° C.

$\nu_{max}$(mull): 1718 cm$^{-1}$.

δ(CDCl$_3$): 1.07 (3H, t, J 7 Hz); 2.02 (3H, s); 2.18 (3H, s); 2.25 (3H, s); 4.14 (2H, q, J 7 Hz); 5.37 (2H, s); 5.86 (1H, s; 6.70 (1H, s); 7.27 (5H, s).

(Found: C, 68.96; H, 6.53; N, 11.41; C$_{21}$H$_{23}$N$_3$O$_3$ requires C, 69.02; H, 6.34; N, 11.50%).

M+ 365.1768 (C$_{21}$H$_{23}$N$_3$O$_3$).

(b) Ethyl 5-(2,3,5-trimethylphenoxy)-1H-v-triazole-4-carboxylate

Hydrogenation of a solution of ethyl 1-benzyl-5-(2,3,5-trimethylphenoxy)-v-triazole-4-carboxylate (13.0 g), in ethanol (300 cm$^3$) using 10% palladinized charcoal (1.0 g) for 2 hours at 100° C. and 1000 psi afforded 8.60 g (88%) of the debenzylated material of mp (ethanol/water) 98° C.

$\nu_{max}$(mull): 1700, 3150, 3523 cm$^{-1}$.

δ(CDCl$_3$): 1.30 (3H, t, J 7 Hz); 2.10 (3H, s); 2.22 (6H, s); 4.37 (2H, q, J 7 Hz); 6.70 (1H, s); 6.79 (1H, s); 7.15 (1H, br, exchangeable proton).

M+ 275.1278 (C$_{14}$H$_{17}$N$_3$O$_3$).

(Found: C, 58.91; H, 6.59; N, 13.80, C$_{14}$H$_{17}$N$_3$O$_3$½H$_2$O requires: C, 59.15; H, 6.38; N, 14.78%).

(c) 5-(2,3,5-Trimethylphenoxy)-1H-v-triazole-4-carboxylic acid

A solution of ethyl 5-(2,3,5-trimethylphenoxy)-1H-v-triazole-4-carboxylate (8.0 g; 0.03 mole) in 1.25 M aqueous sodium hydroxide solution (100 cm$^3$; 0.12 mole) was stirred overnight at 70° C. and then cooled. Acidification gave a white precipitate which was filtered off, washed well with water and dried to give 7.0 g crude material. Recrystallised from ethanol/water to give 4.0 g (60%) of white solid, mp 145° C. (d).

$\nu_{max}$(mull): 1757, 3250 cm$^{-1}$.

$\delta$(CD$_3$)$_2$SO: 2.08 (3H,s); 2.18 (3H,s); 2.22(3H,s); 6.62 (1H,s) 6.81 (1H,s).

$\lambda_{max}$ (ethanol) 246 nm ($\epsilon$=5200).

M$^+$ 247.0969 (C$_{12}$H$_{13}$N$_3$O$_3$).

(Found: C,58.80; H, 5.64; N, 16.48: C$_{12}$H$_{13}$N$_3$O$_3$ requires: C, 58.29; H, 5.30; N, 17.00%).

(d) 9-oxo-5,6,8-Trimethyl-1H,9H-benzopyrano[2,3-d]-v-triazole

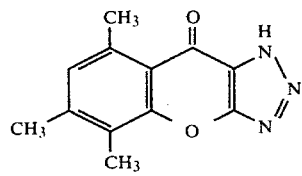

A solution of methanesulphonic acid (20 cm$^3$) and phosphoric oxide (8.0 g) was stirred at 60° C. 5-(2,3,5-Trimethylphenoxy)-1H-v-triazole-4-carboxylic acid (1.0 g) was added and the solution stirred at 60° C. for 28 hours then cooled. The reaction was diluted with water (125 cm$^3$) and the white precipitate filtered and washed with water to yield 0.75 g (81%) of the benzopyranotriazole, mp (ethanol) 268°-269° C. (d).

$\nu_{max}$(mull): 1610, 1660, 3270 cm$^{-1}$.

$\delta$(CD$_3$)$_2$SO: 2.38 (6H, s); 2.75 (3H,s); 6.98 (1H,s); $\lambda_{max}$ (ethanol) 226 nm ($\epsilon$=22,300),277 nm ($\epsilon$=15,200), 319 nm ($\epsilon$=6,500).

M$^+$ 229.0865 (C$_{12}$H$_{11}$N$_3$O$_2$).

Found: C, 62.87; H, 5.09; N, 18.41; C$_{12}$H$_{11}$N$_3$O$_2$ requires: C, 62.87; H, 4.84; N, 18.33%).

EXAMPLE 8

(a) Ethyl 5-hydroxy-1-(4-methoxybenzyl)-v-triazole-4-carboxylate

To a stirred solution of sodium (6.03 g; 0.26 mole) in ethanol (450 ml) was added diethyl malonate (41.9 g; 0.26 mole). After 30 minutes a solution of 4-methoxybenzyl azide (42.5 g; 0.26 mole) in ethanol (50 ml) was added dropwise to the stirred solution and the mixture gently refluxed for 18 hours. After cooling, the bulk of the ethanol was removed in vacuo and water added. Acidification gave a crystalline precipitate of the title compound which was filtered off, washed with water and dried. Recrystallization from chloroform-petrol ether (40°-60°) gave 47.7 g (67%) of product of mp 117° C.

(Found: C, 56.41; H, 5.74; N, 15.02; C$_{13}$H$_{15}$N$_3$O$_4$ requires: C, 56.31; H, 5.45; N, 15.15%).

(b) Ethyl 5-chloro-1-(4-methoxybenzyl)-v-triazole-4-carboxylate

Phosphorous pentachloride (30 g; 0.144 mole) was added to a stirred solution of ethyl 5-hydroxy-1-(4-methoxybenzyl)-v-triazole-4-carboxylate (37 g; 0.133 mole) in dry toluene (400 ml) and the mixture was warmed to 40° (oil bath temperature) for 90 minutes. The solvent was evaporated in vacuo and the residue taken up in ether and washed well with saturated aqueous sodium bicarbonate solution and water. Evaporation of the dried organic phase gave an oil from which the chloro compound, 18 g (46%) of mp 74° C. was isolated by crystallization from ether-petrol (40°-60°).

(Found; C, 52.59; H, 4.68; N, 13.90; Cl, 11.96; C$_{13}$H$_{14}$ClN$_3$O$_3$ requires: C, 52.79; H, 4.77; N, 14.21; Cl, 11.99%).

(c) Ethyl 1-(4-methoxybenzyl)-5-phenoxy-v-triazole-4-carboxylate

Sodium hydride (1.63 g; 0.034 mole of a 50% dispersion of mineral oil) was added to a solution of phenol (3.18 g; 0.034 mole) in dry DMF (80 ml) and the mixture stirred at room temperature for 30 minutes. Ethyl 5-chloro-1-(4-methoxybenzyl)-v-triazole-4-carboxylate (10 g; 0.034 mole) was added to this solution and the mixture stirred at 70° C. for 20 hours. The solvent was removed in vacuo and the residue partitioned between water and ethyl acetate. The organic phase was washed with 5% sodium hydroxide solution then water and dried (MgSO$_4$). Evaporation gave 10.22 g (82%) of the product which after recrystallization from ethanol-water had mp 62°-63° C.

$\nu_{max}$ (mull) 1720, 1608, 1595, 1570, 1550, 1515 cm$^{-1}$.

$\delta$(CDCl$_3$): 1.02 (3H, t, J 7 Hz); 3.70 (3H, s); 4.12 (2H, q, J 7 Hz); 5.33 (2H, s); 6.98 (9H, m).

(Found: C, 64.31; H, 5.56; N, 11.98; C$_{19}$H$_{19}$N$_3$O$_4$ requires: C, 64.61; H, 5.42; N, 11.90%).

(d) 1-(4-Methoxybenzyl)-5-phenoxy-v-triazole-4-carboxylic acid

Hydrolysis of ethyl 1-(4-methoxybenzyl)-5-phenoxy-v-triazole-4-carboxylate (7.77 g) as described in example 1a gave 6.56 g (90%) of the acid of mp (ether-petrol[40°-60°]) 125°-216° C. (dec.).

$\nu_{max}$ (mull) 3540, 3300, 3200, 2650 (broad) 1715 cm$^{-1}$.

$\delta$ (DMSO); 3.73 (3H,s); 5.40 (2H, s); 7.07 (9H, complex m) low field broad exchangeable proton.

(Found: C, 62.54; H, 4.95; N, 13.00; C$_{17}$H$_{15}$N$_3$O$_4$ requires: C, 62.76; H, 4.65; N, 12.92%).

(e) 3-(4-Methoxybenzyl)-9-oxo-9H-benzopyrano[2,3-d]-v-triazole

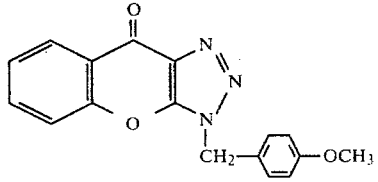

Thionyl chloride (45 ml) containing 1-(4-methoxybenzyl)-5-phenoxy-v-triazole-4-carboxylic acid (3.9 g; 0.012 mole) was refluxed for 90 minutes and the excess thionyl chloride removed in vacuo. The crude acid chloride so obtained was redissolved in dry dichloromethane (100 ml) and anhydrous powdered aluminium chloride (5 g) added in portions with stirring. After 1 hour at ambient temperature the reaction mixture was poured into ice-water and the phases separated. Evaporation of the dried (MgSO$_4$) organic phase gave an oily solid which afforded the title compound on trituration with ether. Recrystallization from ethanol gave 1.30 g (35%) of mp 175° C.

$\nu_{max}$ (mull); 1685, 1605 cm$^{-1}$.

δ(CDCl$_3$; DMSO): 3.78 (3H,s); 5.64 (2H, s); 6.82–7.80 (7H, complex m); 8.40 (1H, m).

(Found: C, 66.55; H, 4.61; N, 12.86; C$_{17}$H$_{13}$N$_3$O$_3$ requires C, 66.44; H, 4.26; N, 13.68%).

(f) 9-Oxo-1H,9H-benzopyrano[2,3-d]-v-triazole

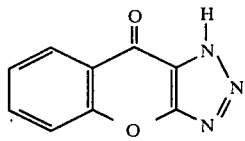

A solution of 3-(4-methoxybenzyl)-9-oxo-9H-benzopyrano[2,3-d]-v-triazole (0.40 g) in trifluoroacetic acid (5 ml) was stirred at 40° C. until the signal at δ5.64 in the nmr spectrum disappeared (ca 3 hours). Addition of a little water produced a dark solid which was removed by filtration. Further addition of water precipitated the title compound, 0.17 g (70%) which was identical with authentic material by mp, ir and ms.

EXAMPLE 9

(a) Ethyl 5-(4-fluorophenoxy)-1-(4-methoxybenzyl)-v-triazole-4-carboxylate

To a stirred solution of 4-fluorophenol (2.27 g; 0.02 mole) in dry DMF (30 ml) was added a 50% dispersion of NaH in mineral oil (0.97 g; 0.02 mole). The mixture was stirred for 1 hour then ethyl 5-chloro-1-(4-methoxybenzyl)-v-triazole-4-carboxylate (5.91 g; 0.02 mole) was added and the mixture stirred at 80° C. for 20 hours. After cooling the DMF was removed in vacuo and the residue partitioned between ethyl acetate and water. The organic phase was washed with 10% sodium hydroxide solution and water and dried (MgSO$_4$). Evaporation of the solvent gave 6.38 g (82%) of crude product of mp 75° C. Recrystallization from aqueous ethanol gave mp 81°–82° C.

$\nu_{max}$ (mull): 1738, 1720 cm$^{-1}$.

δ(CDCl$_3$): 1.11 (3H, t, J 8 Hz); 3.73 (3H, s); 4.16 (2H, q, J 8 Hz); 5.34 (2H, s); 6.70–7.30 (8H, m).

(Found: C, 61.70; H, 4.65; N, 11.26; C$_{19}$H$_{18}$N$_3$FO$_4$ requires: C, 61.45; H, 4.89; N, 11.32%).

(b) 5-(4-Fluorophenoxy)-1-(4-methoxybenzyl)-v-triazole-4-carboxylic acid

Hydrolysis of ethyl 5-(4-fluorophenoxy)-1-(4-methoxybenzyl)-v-triazole-4-carboxylate (5.0 g: 0.014 mole) with 1.25 M aqueous sodium hydroxide as described in example 1a gave 4.56 g (99%) of product. Extraction into chloroform, filtration and evaporation of solvent gave, after re-crystallization from ethanol, material of melting point 135° C.

$\nu_{max}$ (mull): 1580, 1615, 1695 cm$^{-1}$.

δ(CDCl$_3$): 3.75 (3H, s); 5.33(2H,s); 6.70–7.50 (8H, m); 9.80 (1H, very br, exchangeable with D$_2$O).

(Found: C, 59.54; H, 4.09; N, 12.26; C$_{17}$H$_{14}$FN$_3$O$_4$ requires: C, 59.47; H, 4.11; N, 12.24%). M+ 343.0973, (C$_{17}$H$_{14}$FN$_3$O$_4$).

(c) 7-Fluoro-3-(4-methoxybenzyl)-9-oxo-9H-benzopyrano[2,3-d]-v-triazole

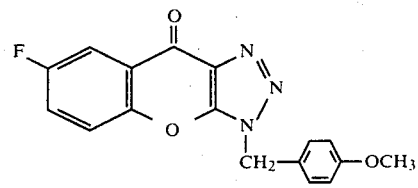

5-(4-Fluorophenoxy)-1-(4-methoxybenzyl)-v-triazole-4-carboxylic acid (0.5 g) was dissolved in thionyl chloride (5 ml) and the solution refluxed for 90 minutes. After cooling, the excess thionyl chloride was removed in vacuo and the residue dissolved in dry dichloromethane (10 ml). Anhydrous aluminium chloride (0.7 g) was added to the stirred chilled solution and the red mixture stirred for 1 hours at ambient temperature. The total was poured into ice-water and the phases separated. From the organic phase the title compound was isolated. It has mp 180°–185° C.

$\nu_{max}$ (mull): 1695 cm$^{-1}$.

δ(DMSO): 3.74 (3H, s); 5.69 (2H, s); 7.15 (4H, AB quartet J 10 Hz; Δ$\nu$=40 Hz); 7.50–8.20 (3H, m) M+325.0867 corresponding to C$_{17}$H$_{12}$FN$_3$O$_3$.

(d) 7-Fluoro-9-oxo-1H,9H-benzopyrano[2,3-d]-v-triazole

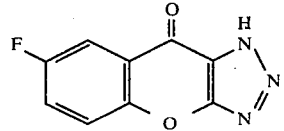

Deprotection of 7-fluoro-3-(4-methoxybenzyl)-9-oxo-9H-benzopyrano[2,3-d]triazole with trifluoroacetic acid as described above afforded the title compound of mp 265°–268° C. (dec.).

$\nu_{max}$ (mull) 3170, 1645 cm$^{-1}$.

δ(DMSO): 5.30 (3H, broad exchangeable NH+H$_2$O); 6.80–7.30 (3H, m).

Passive Cutaneous Anaphylaxis (PCA)

Serum containing heat-labile homocytotropic antibody was raised in rats to crystallized ovalbumin XOA by the method of Mota (I. Mota, Immunology, 7, 681, (1964)) using Bordettela pertussis vaccine as adjuvant.

Passive cutaneous anaphylaxis (PCA) was carried out by a method based on that of Ovary and Bier, (A. Ovary and O. G. Bier, Proc. Soc. Exp. Bio. Med 81, 584, (1952)) as modified by Goose and Blair. (Immunology 16, 749 (1969)).

Male Wistar rats of 250–300 g were give 0.1 ml of each of six twofold serial dilutions of pooled antiserum in 0.9% saline injected intradermally into separate sites in their shaved backs. Later (72 hours) the animals were challenged by intravenous injection of 0.3 ml of a 1% solution of ovalbumin in an isotonic solution of saline buffered with 0.05 M, pH 7.2, Sorenson Buffer (PBS), mixed with 0.2 ml of a 5% solution of Pontamine Sky Blue (6BX C.I. 24410, Raymond A. Lamb, London) in isotonic saline. The rats were killed after 20 minutes and the diameter of the blue wheals at the antibody injection sites was measured on the outer surface of the skin. The starting dilution of the serum was adjusted so that there was no response, after challenge, at the injection site of the highest dilution and a maximum response at the lowest dilutions. Typically six twofold serial dilutions of the serum from ¼ to 1/128 were used.

Compounds were tested for their ability to reduce the diameter of the wheals at those intradermal sites which in control animals gave less than maximum response. Each dose of the compound was administered to six rats at a measured time prior to intravenous challenge with ovalbumin. Control groups of six rats were given the same volume (0.2 ml: 100 g$^{-1}$) of carrier fluid at the same time prior to the challenge.

The results were calculated as follows: % inhibition of PCA = 100 (1−a/b) where a = the sum of the diameters of the wheals produced in the test animal at the sites of antibody dilutions as used in control groups and b = the mean sum of the diameters of the wheals produced in the control group of animals at those antibody sites where at least five out of six of the animals gave less than maximum response. A typical variation in the control group of animals was SEM ±6%.

| Compound of | Route | Carrier Fluid | Time* (mins) | Dose mg/kg | % Inhibitions of rat PCA |
|---|---|---|---|---|---|
| Example 1 | S.C. | PBS with | 10 | 10 | 83 |
|  |  | Na HCO$_3$ | 30 | 10 | 29 |
| Example 3 | S.C. | PBS with | 10 | 10 | 78 |
|  |  | NaHCO$_3$ | 30 | 10 | 41 |
| Example 4 | S.C. | PBS with | 10 | 20 | 66 |
|  |  | NaHCO$_3$ | 30 | 20 | 35 |
| Example 5 | S.C. | PBS with | 10 | 20 | 64 |
|  |  | NaHCO$_3$ | 30 | 20 | 14 |
| Example 6d | S.C. | PBS with | 10 | 5 | 72 |
|  |  | NaHCO$_3$ | 30 | 5 | 22 |
| Example 6e | S.C. | PBS with | 10 | 5 | 86 |
|  |  | NaHCO$_3$ | 30 | 5 | 45 |
| Example 7 | S.C. | PBS with | 10 | 10 | 40 |
|  |  | NaHCO$_3$ | 30 | 10 | 18 |

*Time between administration of compound and antigen challenge.

Toxicity

No toxic effects were observed in any of the tests reported above.

The LD$_{50}$ of the compound of Example 6 (d) is between 20 to 80 mg/kg i.v. and between 125 to 500 mg/kg per os, in mice.

What we claim is:

1. A compound selected from the group consisting of a benzopyranotriazole of the formula:

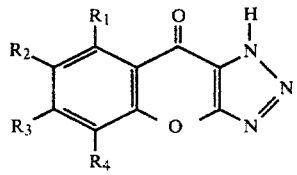

and pharmaceutically acceptable salts thereof, wherein each of R$_1$, R$_2$, R$_3$ and R$_4$ taken independently of the others is hydrogen, halo, nitro, lower alkyl or lower alkoxy, or any adjacent two of R$_1$, R$_2$, R$_3$ and R$_4$ taken together are alkylene of from 3 to 5 carbon atoms or 1,4buta-1,3-dienylene.

2. A compound according to claim 1, wherein each of R$_1$, R$_2$, R$_3$ and R$_4$ is hydrogen, methyl, ethyl, n-propyl, methoxy, ethoxy, n-propoxy, fluoro or chloro.

3. A compound according to claim 2 wherein at least one of R$_1$, R$_2$, R$_3$ and R$_4$ is hydrogen.

4. A compound according to claim 3, wherein two of R$_1$, R$_2$, R$_3$ and R$_4$ are hydrogen.

5. A compound according to claim 4 wherein each of R$_1$ and R$_4$ is hydrogen, and each of R$_2$ and R$_3$ independently of the other is methyl, ethyl or n-propyl.

6. A compound according to claim 1 which is the sodium salt.

7. 6,7-Dimethyl-9-oxo-1H,9H-benzopyrano[2,3-d]-v-triazole.

8. The compound according to claim 7 which is the sodium salt.

9. 7,8-Dimethyl-9-oxo-1H,9H-benzopyran[2,3-d]-v-triazole.

10. The compound according to claim 9 which is the sodium salt.

11. A pharmaceutical composition comprising an antiallergically effective amount of a compound according to claim 1 and a pharmaceutically acceptable carrier.

12. A compound of the formula:

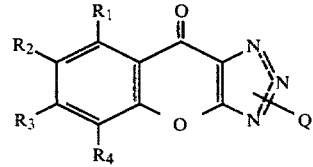

wherein each of R$_1$, R$_2$, R$_3$ and R$_4$ taken independently of the others is hydrogen, halo, nitro, lower alkyl or lower alkoxy, or any adjacent two of R$_1$, R$_2$, R$_3$ and R$_4$ taken together are alkylene of from 3 to 5 carbon atoms or ,4-buta-1,3-dienylene, and Q is benzyl substituted with alkoxy of 1 to 6 carbon atoms.

* * * * *